(12) United States Patent
Nevala et al.

(10) Patent No.: US 12,029,280 B2
(45) Date of Patent: Jul. 9, 2024

(54) APPARATUS, A SYSTEM AND A METHOD OF FOOT MEASUREMENT FOR SELECTING READY-MADE FOOTWEAR

(71) Applicant: Right size company Oy, Pomarkku (FI)

(72) Inventors: Tero Nevala, Tampere (FI); Jarno Fonsén, Pärnu (EE)

(73) Assignee: RIGHT SIZE COMPANY OY, Pomarkku (FI)

( * ) Notice: Subject to any disclaimer, the term of this patent is extended or adjusted under 35 U.S.C. 154(b) by 389 days.

(21) Appl. No.: 17/594,333

(22) PCT Filed: Apr. 3, 2020

(86) PCT No.: PCT/FI2020/050221
§ 371 (c)(1),
(2) Date: Oct. 12, 2021

(87) PCT Pub. No.: WO2020/208298
PCT Pub. Date: Oct. 15, 2020

(65) Prior Publication Data
US 2022/0183424 A1    Jun. 16, 2022

(30) Foreign Application Priority Data

Apr. 12, 2019   (FI) ...................... 20195301

(51) Int. Cl.
*A43D 1/02*    (2006.01)
(52) U.S. Cl.
CPC ............. *A43D 1/025* (2013.01); *A43D 1/027* (2013.01)

(58) Field of Classification Search
CPC ........... A43D 1/02; A43D 1/025; A43D 1/027
USPC ............. 33/3 A, 3 C, 512, 514.1, 514.2, 515
See application file for complete search history.

(56) References Cited

U.S. PATENT DOCUMENTS

| | | | |
|---|---|---|---|
| 4,395,826 A | | 8/1983 | Bidegain et al. |
| 5,164,793 A | | 11/1992 | Wolfersberger et al. |
| 5,414,943 A | * | 5/1995 | Vogt ........................ A61B 5/107 33/759 |
| 5,732,475 A | * | 3/1998 | Sacks .................... A61B 5/1073 33/555.4 |
| 6,460,262 B1 | * | 10/2002 | Cabak ................... A61B 5/1076 33/759 |
| 7,293,370 B2 | * | 11/2007 | Kaplan ..................... A43B 3/26 36/73 |

(Continued)

FOREIGN PATENT DOCUMENTS

| | | |
|---|---|---|
| CN | 203220012 U | 10/2013 |
| CN | 104679857 A | 6/2015 |

(Continued)

*Primary Examiner* — George B Bennett
(74) *Attorney, Agent, or Firm* — Lippes Mathias LLP

(57) ABSTRACT

The invention allows foot measurement for selecting ready-made footwear that provides accurate results efficiently, easily and with low costs, and which can be performed both at home and at stores. An apparatus (120) of foot measurement comprises a base plate (121) and a single circumference measurement loop (123). The base plate (121) is utilized in measuring the length (401) of a foot, and an elastic portion (123A) of the circumference measurement loop (123) is utilized in measuring the circumference (402) around the ball of the foot.

17 Claims, 8 Drawing Sheets

(56) References Cited

U.S. PATENT DOCUMENTS

| | | | |
|---|---|---|---|
| 8,728,012 B2* | 5/2014 | Braido | A61B 5/6876 |
| | | | 33/759 |
| 10,194,837 B2* | 2/2019 | Kanchan | A61B 5/6806 |
| 10,607,507 B2* | 3/2020 | Connor | A61B 5/4866 |
| 10,743,795 B2* | 8/2020 | Morris | A61B 5/6807 |
| 11,176,738 B2* | 11/2021 | Revkov | G06T 15/30 |
| 11,278,453 B2* | 3/2022 | Hitschmann | A61F 5/0109 |
| 2013/0303923 A1* | 11/2013 | Lerner | A61B 5/02208 |
| | | | 600/490 |
| 2017/0169571 A1 | 6/2017 | Hung et al. | |
| 2020/0305765 A1* | 10/2020 | Herr | A61B 5/4523 |
| 2021/0378854 A1* | 12/2021 | Bichler | A61F 5/0127 |
| 2022/0192324 A1* | 6/2022 | Oshima | A43D 1/027 |
| 2023/0255321 A1* | 8/2023 | Smit | G01B 11/02 |
| | | | 33/6 |
| 2024/0041165 A1* | 2/2024 | Kishimoto | A43D 3/025 |

FOREIGN PATENT DOCUMENTS

| | | | |
|---|---|---|---|
| CN | 107305699 A | 10/2017 | |
| EP | 2 896 362 A1 | 7/2015 | |
| GB | 972577 A | 10/1964 | |
| GB | 1512017 A | 5/1978 | |
| GB | 2509696 A | 7/2014 | |
| JP | S63-277001 A | 11/1988 | |
| JP | 2019-055184 A | 4/2019 | |

\* cited by examiner

The French Shoe Size System

| Shoe Size | \ | The Number of Girth | | | | | | | | | Shoe Length in centimeters |
|---|---|---|---|---|---|---|---|---|---|---|---|
| | 4 | 5 | 6 | 7 | 8 | 9 | 10 | 11 | 12 | | |
| | | | The Girth in centimeters | | | | | | | | |
| 48 | 25,4 | 25,9 | 26,4 | 26,9 | 27,4 | 27,9 | 28,4 | 28,9 | 29,4 | | 32 |
| 47 | 25 | 25,5 | 26 | 26,5 | 27 | 27,5 | 28 | 28,5 | 29 | | 31,3 |
| 46 | 24,6 | 25,1 | 25,6 | 26,1 | 26,6 | 27,1 | 27,6 | 28,1 | 28,6 | | 30,6 |
| 45 | 24,2 | 24,7 | 25,2 | 25,7 | 26,2 | 26,7 | 27,2 | 27,7 | 28,2 | | 30 |
| 44 | 23,8 | 24,3 | 24,8 | 25,3 | 25,8 | 26,3 | 26,8 | 27,3 | 27,8 | | 29,3 |
| 43 | 23,4 | 23,9 | 24,4 | 24,9 | 25,4 | 25,9 | 26,4 | 26,9 | 27,4 | | 28,6 |
| 42 | 23 | 23,5 | 24 | 24,5 | 25 | 25,5 | 26 | 26,5 | 27 | | 28 |
| 41 | 22,6 | 23,1 | 23,6 | 24,1 | 24,6 | 25,1 | 25,6 | 26,1 | 26,6 | | 27,3 |
| 40 | 22,2 | 22,7 | 23,2 | 23,7 | 24,2 | 24,7 | 25,2 | 25,7 | 26,2 | | 26,6 |
| 39 | 21,8 | 22,3 | 22,8 | 23,3 | 23,8 | 24,3 | 24,8 | 25,3 | 25,8 | | 26 |
| 38 | 21,4 | 21,9 | 22,4 | 22,9 | 23,4 | 23,9 | 24,4 | 24,9 | 25,4 | | 25,3 |
| 37 | 21 | 21,5 | 22 | 22,5 | 23 | 23,5 | 24 | 24,5 | 25 | | 24,6 |
| 36 | 20,6 | 21,1 | 21,6 | 22,1 | 22,6 | 23,1 | 23,6 | 24,1 | 24,6 | | 24 |
| 35 | 20,2 | 20,7 | 21,2 | 21,7 | 22,2 | 22,7 | 23,2 | 23,7 | 24,2 | | 23,3 |
| 34 | 19,8 | 20,3 | 20,8 | 21,3 | 21,8 | 22,3 | 22,8 | 23,3 | 23,8 | | 22,6 |
| 33 | 19,4 | 19,9 | 20,4 | 20,9 | 21,4 | 21,9 | 22,4 | 22,9 | 23,4 | | 22 |
| 32 | 19 | 19,5 | 20 | 20,5 | 21 | 21,5 | 22 | 22,5 | 23 | | 21,3 |
| 31 | 18,6 | 19,1 | 19,6 | 20,1 | 20,6 | 21,1 | 21,6 | 22,1 | 22,6 | | 20,6 |
| 30 | 18,2 | 18,7 | 19,2 | 19,7 | 20,2 | 20,7 | 21,2 | 21,7 | 22,2 | | 20 |
| 29 | 17,8 | 18,3 | 18,8 | 19,3 | 19,8 | 20,3 | 20,8 | 21,3 | 21,8 | | 19,3 |
| 28 | 17,4 | 17,9 | 18,4 | 18,9 | 19,4 | 19,9 | 20,4 | 20,9 | 21,4 | | 18,6 |
| 27 | 17 | 17,5 | 18 | 18,5 | 19 | 19,5 | 20 | 20,5 | 21 | | 18 |
| 26 | 16,6 | 17,1 | 17,6 | 18,1 | 18,6 | 19,1 | 19,6 | 20,1 | 20,6 | | 17,3 |
| 25 | 16,2 | 16,7 | 17,2 | 17,7 | 18,2 | 18,7 | 19,2 | 19,7 | 20,2 | | 16,6 |
| 24 | 15,8 | 16,3 | 16,8 | 17,3 | 17,8 | 18,3 | 18,8 | 19,3 | 19,8 | | 16 |
| 23 | 15,4 | 15,9 | 16,4 | 16,9 | 17,4 | 17,9 | 18,4 | 18,9 | 19,4 | | 15,3 |
| 22 | 15 | 15,5 | 16 | 16,5 | 17 | 17,5 | 18 | 18,5 | 19 | | 14,6 |
| 21 | 14,6 | 15,1 | 15,6 | 16,1 | 16,6 | 17,1 | 17,6 | 18,1 | 18,6 | | 14 |
| 20 | 14,2 | 14,7 | 15,2 | 15,7 | 16,2 | 16,7 | 17,2 | 17,7 | 18,2 | | 13,3 |
| 19 | 13,8 | 14,3 | 14,8 | 15,3 | 15,8 | 16,3 | 16,8 | 17,3 | 17,8 | | 12,6 |
| 18 | 13,4 | 13,9 | 14,4 | 14,9 | 15,4 | 15,9 | 16,4 | 16,9 | 17,4 | | 12 |
| 17 | 13 | 13,5 | 14 | 14,5 | 15 | 15,5 | 16 | 16,5 | 17 | | 11,3 |

600

FIG. 6

APPARATUS, A SYSTEM AND A METHOD OF FOOT MEASUREMENT FOR SELECTING READY-MADE FOOTWEAR

This application is a National Stage Entry of International Application No. PCT/FI2020/050221, filed Apr. 3, 2020, and entitled "AN APPARATUS, A SYSTEM AND A METHOD OF FOOT MEASUREMENT FOR SELECTING READY-MADE FOOTWEAR;" which claims priority to Finland Application No. 20195301, filed Apr. 12, 2019, and entitled "AN APPARATUS, A SYSTEM AND A METHOD OF FOOT MEASUREMENT FOR SELECTING READY-MADE FOOTWEAR," the contents of which are incorporated by reference herein.

BACKGROUND OF THE INVENTION

Field of the Invention

The present application generally relates to foot measurement. In particular, the present application relates to foot measurement to allow accurate selection of ready-made shoes or footwear.

Description of the Related Art

Over the years, shoemakers have developed and optimized shoe lasts to represent the inner space of a shoe in a way that fits as large a portion of general populace as possible. As a result, the proportions of various shoe lasts around the world nowadays tend to fit as much as approximately 80% of the general populace.

These various shoe lasts and their proportions provide a basis for the shoe sizing systems or charts that are used today. Examples of these shoe sizing systems or charts include the French shoe sizing chart and the English shoe sizing chart.

Generally speaking, the shoemaking industry is comprised of manufacturing ready-made (or industrial or non-tailored) footwear and manufacturing tailored, i.e. personalized footwear.

For ready-made footwear, a purchaser needs to either try on footwear samples in a shop or the like to find a fitting size, or when physical samples are not available (such as with Internet shopping), to measure his/her foot accurately enough to allow determining a best-fitting size.

Traditionally, foot measurement has been performed by hand, using e.g. a cobbler's or shoemaker's tape measure. For example, it is possible to measure length of a foot and express the measurement result in centimeters or in different sizing systems. Correspondingly it is possible to measure the width of the same foot and express if a wide or narrow fit should be chosen. However, foot measurement by hand requires experience and skill to provide accurate results. Also, foot measurement by hand is often considered cumbersome and too time consuming by modern Internet shoppers and the like.

More advanced systems may include a scanning device that scans the foot by using a laser scanner or other machine vision tools. These systems are typically quite complicated and expensive and thus, typically it is only possible to have such a device in larger stores or specialists who have a justification for the investment. Also, there are systems that aim to build a three-dimensional (3D) model of the foot e.g. via capturing a multitude of images of the foot from different angles. Again, such systems are complicated and expensive, and typically also difficult and/or time-consuming to use.

As a result, particularly in case of Internet shopping, the person buying new footwear is not visiting any store for measuring or consultation but tries to guess the correct size based on his/her own knowledge and/or past experience and without possibility to try the product before placing an order. In recent years, this has led to a significant rise in the amount of returns of ordered products when the shopper receives the product and finds out that it does not fit after all. Since the returned and tried-at-home footwear are now non-marketable, they represent a significant loss to the shoemaking industry worldwide.

Accordingly, there is a need for foot measurement for selecting ready-made footwear that provides accurate results efficiently, easily and with low costs, and which can be performed both at home and at stores and the like.

SUMMARY OF THE INVENTION

An embodiment of an apparatus of foot measurement comprises a base plate that is configured to receive a foot to be measured. The foot has a first length from a tip of a longest toe to a back of a heel and a first circumference around a ball of the foot. The base plate has a front end and a back end that are at a first distance from each other. The first distance is larger than the first length. The back end of the base plate is configured to receive the back of the heel of the foot to be measured in order to enable determination of the first length based on the first distance and a second distance between the front end of the base plate and the tip of the longest toe of the positioned foot.

The apparatus further comprises a single circumference measurement loop. The circumference measurement loop comprises a first portion of elastic material and a second portion of substantially non-elastic material. When the first portion is non-stretched, the circumference measurement loop has a second circumference that is smaller than the first circumference. The circumference measurement loop is configured to encircle the foot to be measured at its ball in order to enable determination of the first circumference based on the amount of stretch of the first portion.

In an embodiment, alternatively or in addition to the above-described embodiments, the first portion of the circumference measurement loop has a first visual characteristic and the second portion of the circumference measurement loop has a second visual characteristic, the first visual characteristic being visually distinguishable from the second visual characteristic.

In an embodiment, alternatively or in addition to the above-described embodiments, the first and second visual characteristics comprise at least one of contrast, color, brightness or patterning.

In an embodiment, alternatively or in addition to the above-described embodiments, the base plate comprises one or more coordination markers to assist in at least one of the determination of the first length or the determination of the first circumference.

In an embodiment, alternatively or in addition to the above-described embodiments, the apparatus further comprises a heel support provided at the back end of the base plate to assist in positioning the foot to be measured on the base plate.

An embodiment of a system of foot measurement comprises the apparatus of foot measurement according to any of the above described embodiments. The system further comprises a digital camera that is configured to capture an image of a foot positioned on the apparatus. The image covers at least the stretched first portion of the circumference measurement loop and the second distance.

The system further comprises a computing device that comprises at least one processor and at least one memory comprising computer program code. The at least one memory and the computer program code are configured to, with the at least one processor, cause the computing device to at least:
- obtain information about the first distance, the second circumference and a non-stretched length of the first portion;
- receive the captured image;
- identify the second distance and a stretched length of the first portion from the received image;
- determine the first length based on a difference between the obtained first distance and the identified second distance; and
- determine the first circumference based on a sum of the obtained second circumference and a difference between the obtained non-stretched length of the first portion and the identified stretched length of the first portion.

In an embodiment, alternatively or in addition to the above-described embodiments, the at least one memory and the computer program code are further configured to, with the at least one processor, cause the computing device to:
- access a predetermined shoe sizing chart;
- compare the determined first length and first circumference to corresponding data in the accessed shoe sizing chart; and
- determine a shoe size for the foot based on the comparison.

In an embodiment, alternatively or in addition to the above-described embodiments, the at least one memory and the computer program code are further configured to, with the at least one processor, cause the computing device to:
- in identifying the stretched length of the first portion, utilize the difference between the first visual characteristic of the first portion of the circumference measurement loop and the second visual characteristic of the second portion of the circumference measurement loop to distinguish the first portion from the second portion.

An embodiment of a method of foot measurement comprises obtaining, by a computing device, information about a first distance, a second circumference and a non-stretched length of a first portion of the apparatus of foot measurement according to any of the above described embodiments.

The method further comprises receiving, at the computing device, an image of a foot positioned on the apparatus captured with a digital camera, the image covering at least the stretched first portion of the circumference measurement loop and the second distance. The method further comprises identifying, by the computing device, the second distance and a stretched length of the first portion from the received image.

The method further comprises determining, by the computing device, the first length based on a difference between the obtained first distance and the identified second distance.

The method further comprises determining, by the computing device, the first circumference based on a sum of the obtained second circumference and a difference between the obtained non-stretched length of the first portion and the identified stretched length of the first portion.

In an embodiment, alternatively or in addition to the above-described embodiments, the method further comprises:
- accessing, by the computing device, a predetermined shoe sizing chart;
- comparing, by the computing device, the determined first length and first circumference to corresponding data in the accessed shoe sizing chart; and
- determining, by the computing device, a shoe size for the foot based on the comparison.

In an embodiment, alternatively or in addition to the above-described embodiments, the identifying of the stretched length of the first portion comprises utilizing the difference between the first visual characteristic of the first portion of the circumference measurement loop and the second visual characteristic of the second portion of the circumference measurement loop to distinguish the first portion from the second portion.

At least some of the embodiments allow foot measurement for selecting ready-made footwear that provides accurate results efficiently, easily and with low costs, and which can be performed both at home and at stores and the like.

Since the apparatus of foot measurement has a simple structure and it can be made of low-cost materials, at least some of the embodiments allow foot measurement for selecting ready-made footwear that provides accurate results with low costs. Furthermore, since the apparatus of foot measurement can be used with a commonly available smartphone with a digital camera, without requiring expensive laser scanners or the like, at least some of the embodiments allow foot measurement for selecting ready-made footwear that provides accurate results with low costs. Furthermore, at least some of the embodiments allow easy and low-cost postal delivery of the apparatus of foot measurement to a customer in flat form e.g. in an envelope or the like, such that the customer can then easily fold it into shape for use. Furthermore, at least some of the embodiments allow distributing the software needed in the disclosed systems and methods of foot measurement via easily available smartphone software distribution systems (such as the various application stores and the like).

Since the disclosed apparatuses, systems and methods of foot measurement require measuring a single circumference metric in addition to measuring the length of the foot, at least some of the embodiments allow foot measurement for selecting ready-made footwear that provides accurate results with efficiency and ease. Furthermore, since the disclosed apparatuses, systems and methods of foot measurement require capturing only a single two-dimensional image with the digital camera, at least some of the embodiments allow foot measurement for selecting ready-made footwear that provides accurate results with efficiency and ease, as well as quickly.

Using only two metrics and still getting accurate results is possible because the chosen metrics are the defining ones in every shoe last and shoe sizing system worldwide. All the other metrics used in a shoe last or shoe sizing system automatically adapt to these chosen two metrics well enough for the purposes of selecting ready-made footwear. For this reason, at least some of the embodiments also allow globally applicable foot measurement for selecting ready-made footwear that provides accurate results.

BRIEF DESCRIPTION OF THE DRAWINGS

The accompanying drawings, which are included to provide a further understanding of the invention and constitute a part of this specification, illustrate embodiments of the invention and together with the description help to explain the principles of the invention. In the drawings:

FIG. 6 illustrates an example chart of a shoe size system; and

Like reference numerals are used to designate like parts in the accompanying drawings.

DETAILED DESCRIPTION OF THE INVENTION

Figure 1:
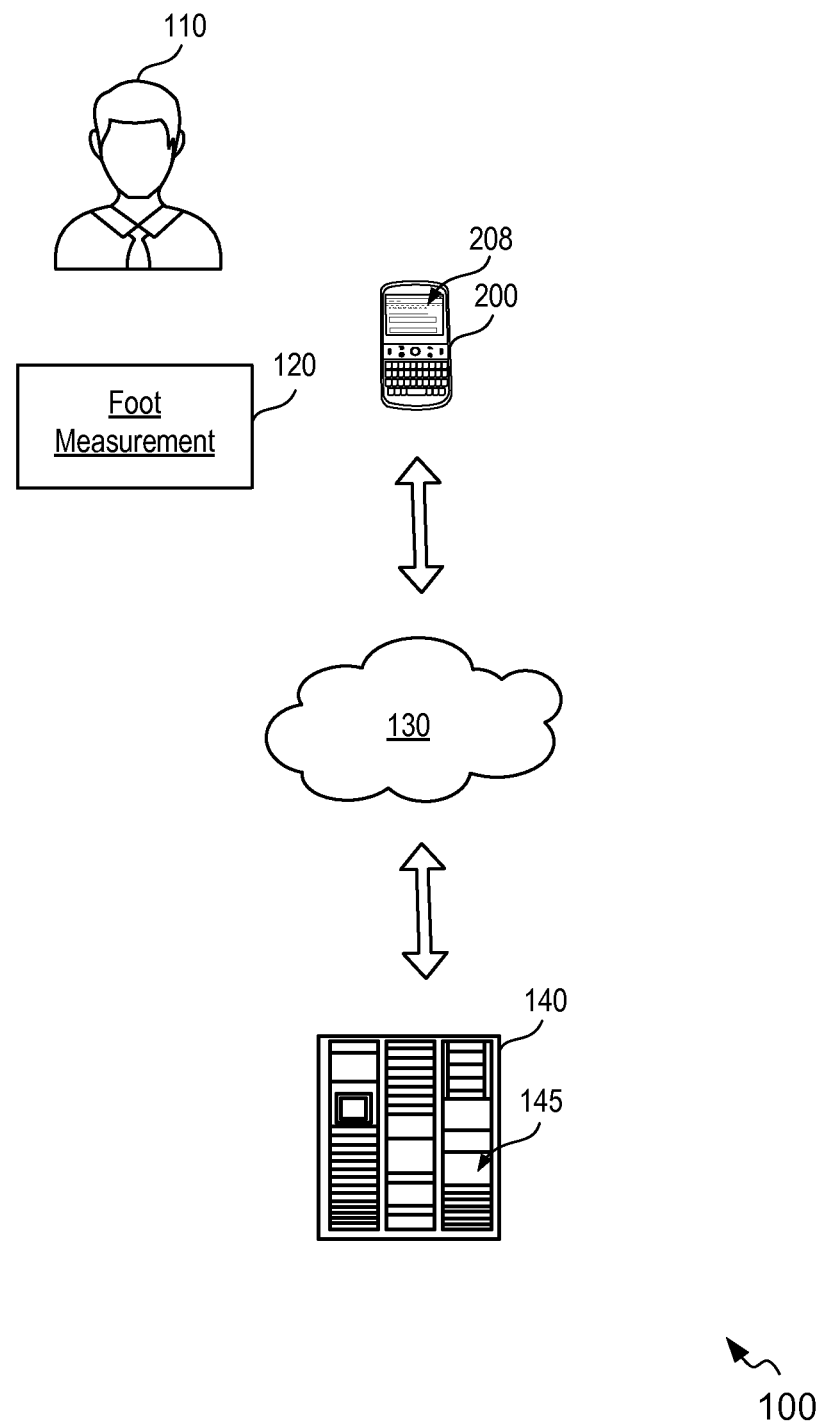
FIG. 1 illustrates an example system, where various embodiments of the present disclosure may be implemented.

Reference will now be made in detail to embodiments of the present invention, examples of which are illustrated in the accompanying drawings. The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

Industrial (or ready-made or non-tailored) footwear or shoes are made with industrial lasts. The last creates the inner volume for the shoe. An industrial last is the result of a long-time evolution. The goal for industrial lasts has been for decades that they would suit and cover as much as possible of the genre that a shoe type is meant for.

It has been found that out of 100% of potential customers, typically approximately 80% of persons have such consistent feet that a normal industrial last shape suits them. The rest, i.e. 20%, consists of two categories: people with such differences and/or problems with their feet that they must seek specially made or orthopedic footwear, and people who are somewhere in between a normal need and an orthopedic need. In other words, normal industrially made shoes are a compromise to serve the normally footed 80%.

Thus, the shoes in normal shoe shops are meant for normally footed customers and the basic shapes are a result of this evolution. The basic shape of an industrial last is graded to different sizes by choosing one of known standard sizing systems which chart the way length and girth grows from size to size.

The shoes are produced on the last and delivered to shops. A customer visits a shop looking for a style and size. A style is something he/she likes, and the size is something he/she thinks might fit his/her foot. By trying several sizes and several styles a shoe is chosen. In practice, the shoe size number can vary depending on the manufacturer and/or country that the product is coming from. This is how the shoe selection process traditionally goes. It is very time and work consuming, and this is a reason why the process is difficult to arrange via Internet.

The customer comes to a decision after being attracted to a shoe type/style and after the length and girth ratio is correct for that particular customer's feet. In regards to length, the shoe must be longer than the foot. The girth measurement, around the ball of the foot, is responsible for the feel and usability of the shoe.

There are three basic types of customers:
1) Standard. Here, the relation between foot length and girth is standard and fits the international last grading/size charts. Shoe selection is easy.
2) Short length/large girth. Here, the main factor is the girth which governs the selection. It is still quite easy to choose shoes. Usually, this type of customer achieves good comfort but has some extra room on the toes due to the fact that he/she had to choose a bigger size due to the measurement in girth.
3) Long length/small girth. Here, the main factor is the length which governs the selection. Usually, this type of customer also achieves good comfort, but the shoe length is as short as possible compared to the foot length. This means that this type of customer has some extra room in the girth.

The above describes how the customer shoe selection process conventionally works among normally footed customers. It is inconvenient, and it is becoming even more so with the internet shopping of shoes.

Figure 7:
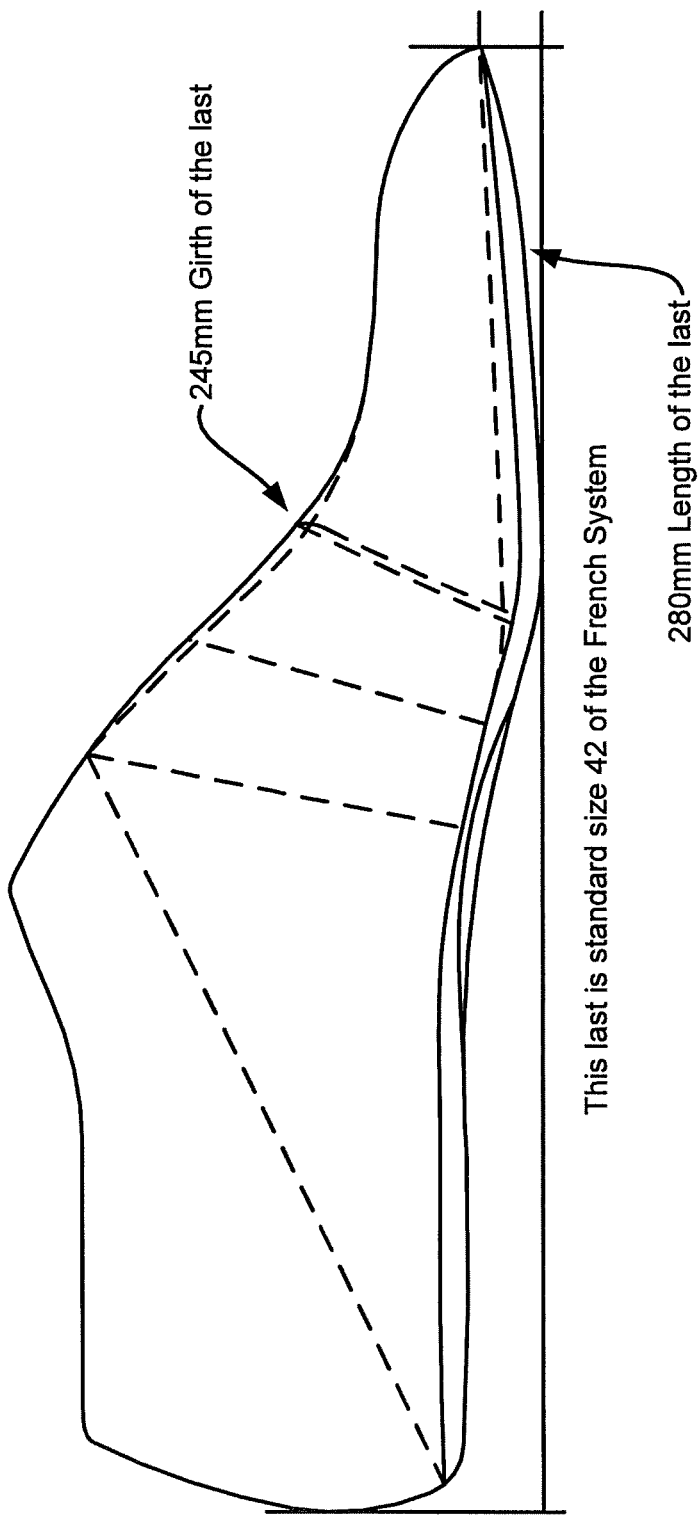
FIG. 7 illustrates an example of a shoe last.

FIG. 7 illustrates an example of a shoe last 700. A shoe last is typically a wooden, plastic or metal form that has multiple functions in the industry. The shoe is designed on the last, and the shoes are produced on the lasts. A last gives the inner volume to the shoe. It is also used in a factory in each process stage. The last also gives the shoe the functionality in use and in the purpose for which the product is intended.

The last represents the knowledge and knowhow of that particular shoe type. It also represents information concerning the type of production, machinery, shoe components and materials used and information about shoe construction and design. For this reason, an industrial shoe last is the result of a long evolution.

A shoe last also represent an image of the foot. Thus, the last is also the result of a long evolution in the sense that the basic shape fits as many persons as possible within the intended customer genre.

In addition to the foot shape, the last has additional shapes that will give room to certain areas (toes etc.). It has aspects from the design (heel height, toe roll and toe shape).

An industrial last is not a "one-off" piece. This would not work since there are so many requirements for it. Instead, an industrial last is a carefully tuned result of long experience.

Industrial shoe lasts have been made for over 150 years. This means that, depending on the style and purpose of the footwear, each company has a good reserve of current and previous lasts that can be modified and fine-tuned by utilizing the evolution of a given last and shoe genre.

Once the basic size of a last is finished, it can be described with size tables for the grading of the last to different lengths and girths. The customer chooses the length and girth via a "shoe size" resulting from these international size tables.

Examples of the size tables include "French system" (also known as "Paris point" and "EU size", example sizes including . . . 41, 42, 43 . . . ), "English sizes" (example sizes including . . . 7, 7½, 8, 8½ . . . ), American sizing, and MondoPoint system. FIG. 6 illustrates an example chart 600 of a shoe size system. More specifically, FIG. 6 illustrates an example chart 600 of the French system. The last illustrated in FIG. 7 is of size "42" in the French system, i.e. it has girth 245 mm and length 280 mm.

These size systems describe for a basic last the way how the last is graded to different lengths and girths. The lengths and girths in the size systems are in millimeters.

Shoe manufacturers use one of these international grading systems for their last. Otherwise they could not use ready-made components (soles, insoles, stiffeners, tools, machinery, etc.) that are offered within the industry. Furthermore, by using these international grading charts the manufacturers can offer their shoes to shoe retailers such that the products will be compatible with other shoes offered by the same retailer.

The following example illustrates the way a customer may choose a shoe from a shoe shop. The example uses the French size system with girth "7". The three example customers below illustrate how a customer chooses a shoe from a given industrial shoe range. They are all normal customers with different length/girth ratios.

| Size number | Lenght mm | | Girth mm | |
| --- | --- | --- | --- | --- |
| 34 | 226.7 | | 213.0 | |
| 35 | 233.3 | | 217.0 | |
| 36 | 240.0 | | 221.0 | |
| 37 | 246.7 | | 225.0 | |
| 38 | 253.3 | "Foot3" | 229.0 | |
| 39 | 260.0 | <259 | 233.0 | |
| 40 | 266.7 | | 237.0 | |
| 41 | 273.3 | "Foot1" | 241.0 | "Foot1, 2 & 3" |
| 42 | 280.0 | <276 | 245.0 | <244 |
| 43 | 286.7 | | 249.0 | |
| 44 | 293.3 | "Foot2" | 253.0 | |
| 45 | 300.0 | <294 | 257.0 | |
| 46 | 306.7 | | 261.0 | |
| 47 | 313.3 | | 265 | |

The example customer "Foot1" has length 276 mm and girth 244 mm. Thus, the best fitting size number for this particular model is number "42".

The example customer "Foot2" has length 294 mm and girth 244 mm. Thus, the best fitting size number for this particular model is number "45". In this case, the length is the governing factor whereas the girth will be too loose. The customer lives with this fact or chooses another shoe model that has a different length/girth ratio.

The example customer "Foot3" has length 259 mm and girth 244 mm. Thus, the best fitting size number for this particular model is number "42". In this case, the girth is the governing factor whereas there will be extra room in toes. The customer lives with this fact or chooses another shoe model that has a different length/girth ratio.

The above illustrates how the customer shoe selection conventionally works in a shoe shop and why many pairs will typically have to be fitted in the shop. The above also illustrates the reason why shoe purchasing is difficult to arrange via Internet.

FIG. 1 illustrates an example system 100, where various embodiments of the present disclosure may be implemented. An example representation of the system 100 is shown depicting an apparatus 120 of foot measurement and a computing device 200, both of which may be used by a user 110 to measure his/her foot e.g. in order to find a best-fitting shoe or footwear size from among a selection of standard shoe sizes.

The computing device 200 may comprise a digital camera 208, as shown in the example embodiment of FIG. 1.

Alternatively, the digital camera 208 may be implemented as a unit external to the computing device 200 but communicatively connected to the computing device 200 to allow transfer of captured images from the digital camera 208 to the computing device 200.

The system 100 further comprises a server device 140 which may comprise a database 145 comprising one or more shoe sizing charts. A network 130 may connect the server device 140 and the computing device 200 to each other. The network 130 may be a centralized network or it may comprise a plurality of sub-networks that may offer a direct communication between the entities or may offer indirect communication between the entities. Examples of the network 130 include wireless networks, wired networks, and combinations thereof. Some non-exhaustive examples of wireless networks may include wireless local area networks (WLANs), Bluetooth or Zigbee networks, cellular networks and the like. Some non-exhaustive examples of wired networks may include Local Area Networks (LANs), Ethernet, Fiber Optic networks and the like. An example of a combination of wired networks and wireless networks may include the Internet. Examples of the server device 140 include, but are not limited to, a desktop computer running a service, a laptop computer running a service, and/or a network server running a service.

Figure 2:
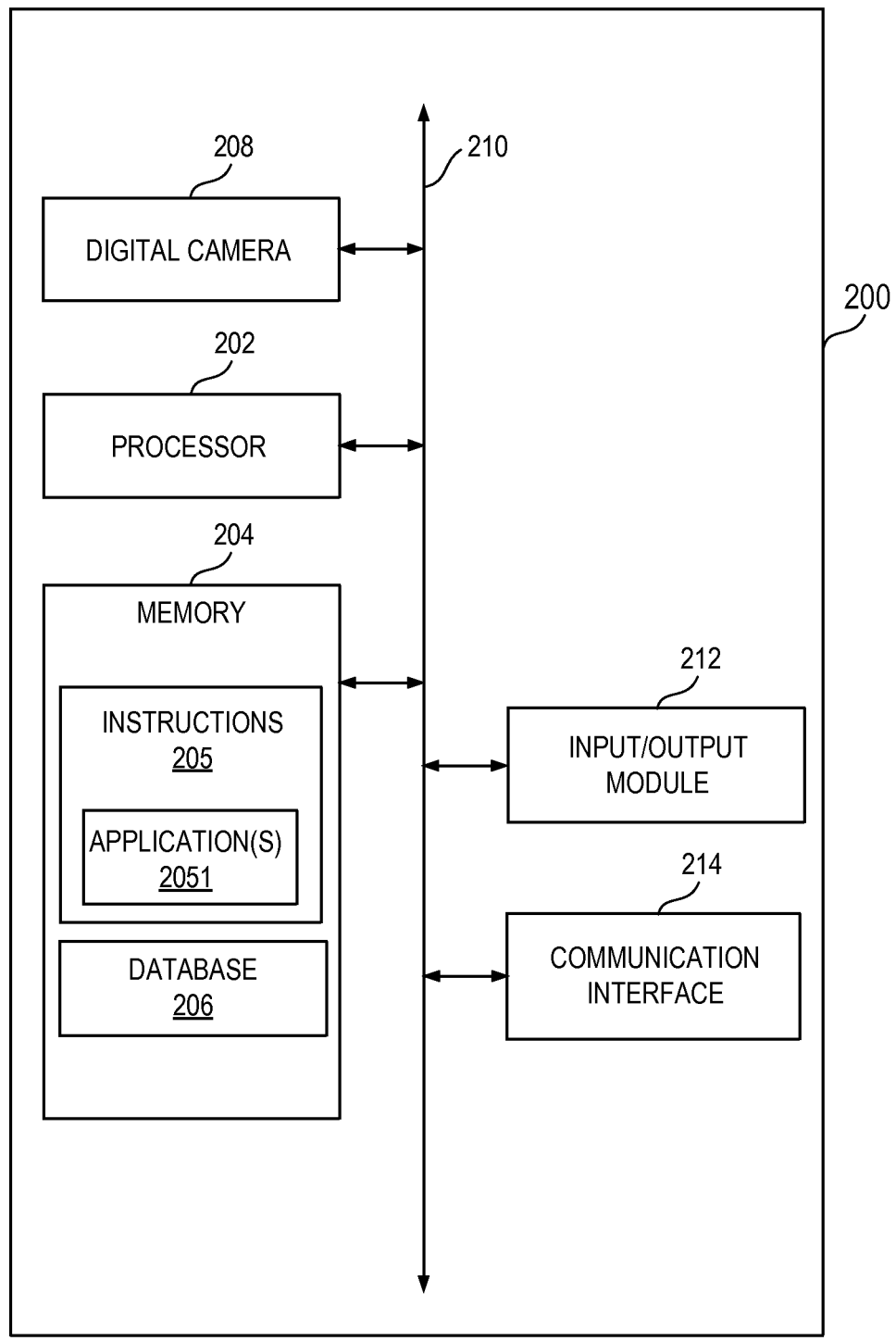
FIG. 2 is a block diagram of a computing device capable of implementing example embodiments described herein.

Alternatively/additionally, the computing device 200 itself may comprise a database 206 that may comprise e.g. one or more shoe sizing charts, as shown in FIG. 2.

The computing device 200 is configured to execute software 205 including a foot measurement application 2051. The computing device 200 may include e.g. a mobile phone, a smartphone, a tablet computer, a smart watch, a wearable device, a smart device, or any hand-held or portable device having capability to run the foot measurement application.

Figure 3A:
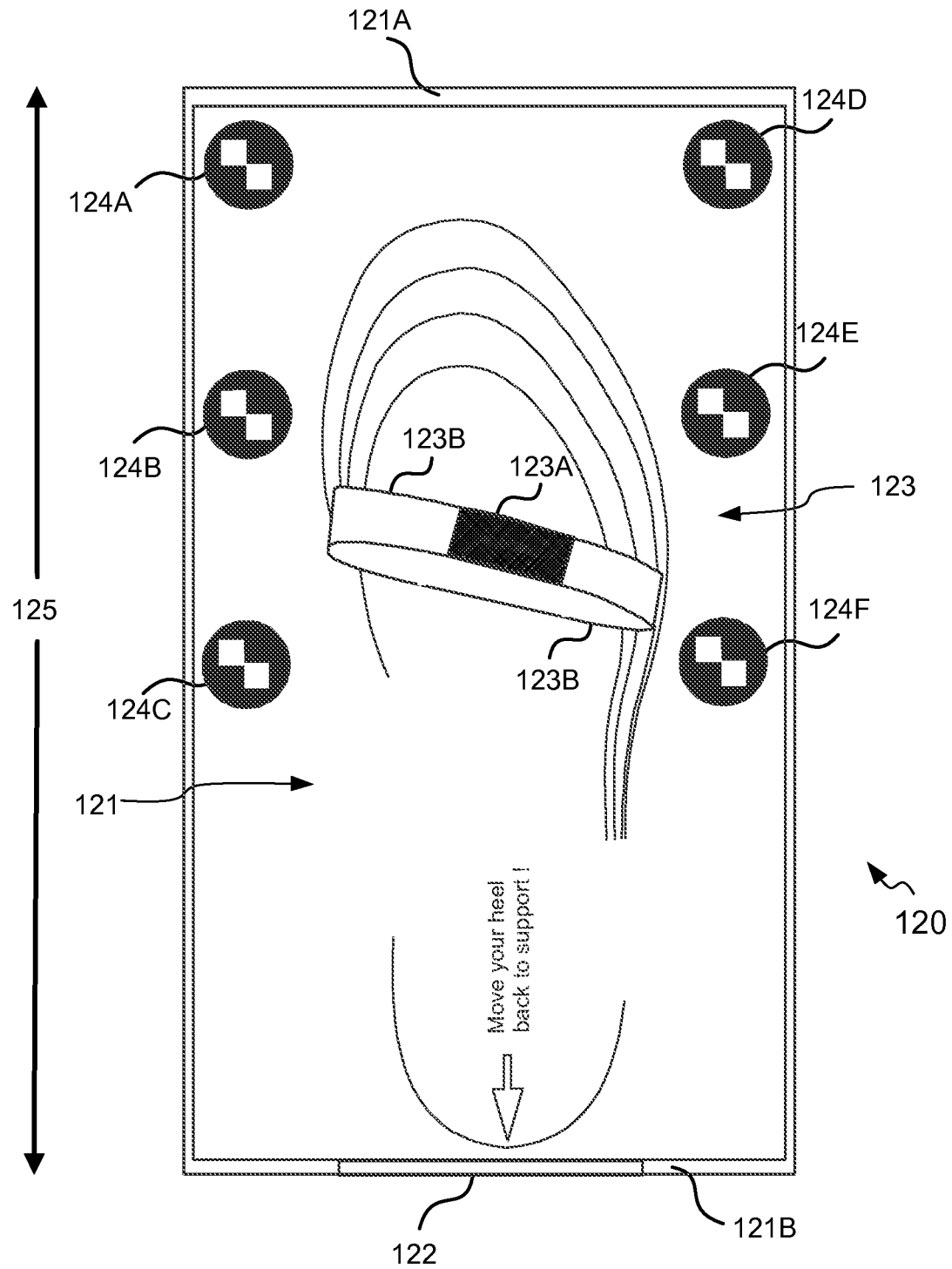
FIG. 3A illustrates a view of an apparatus of foot measurement capable of implementing example embodiments described herein.
Figure 3B:
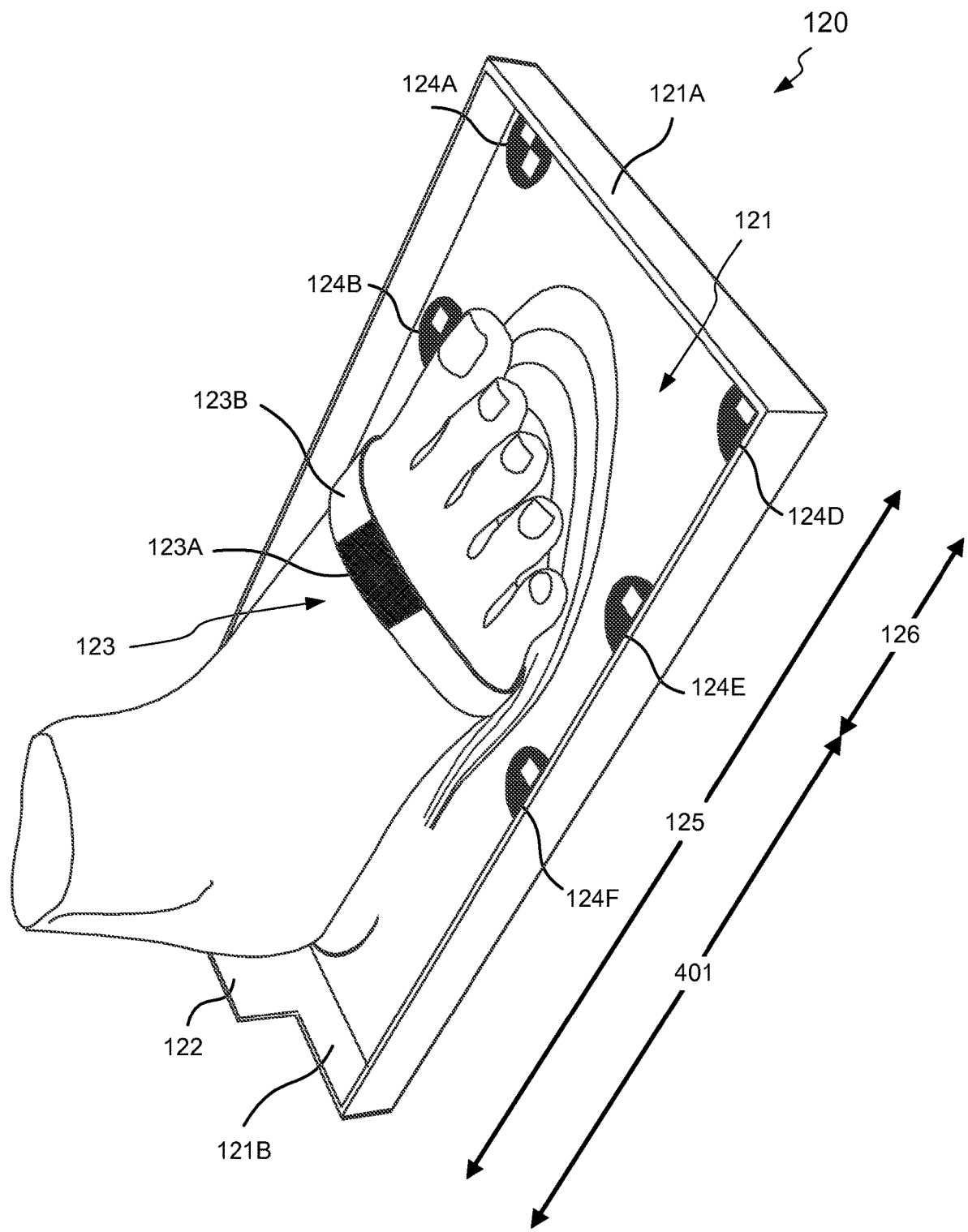
FIG. 3B illustrates another view of an apparatus of foot measurement capable of implementing example embodiments described herein.

FIGS. 3A and 3B illustrate the apparatus 120 of foot measurement capable of implementing example embodiments described herein.

Figure 4:
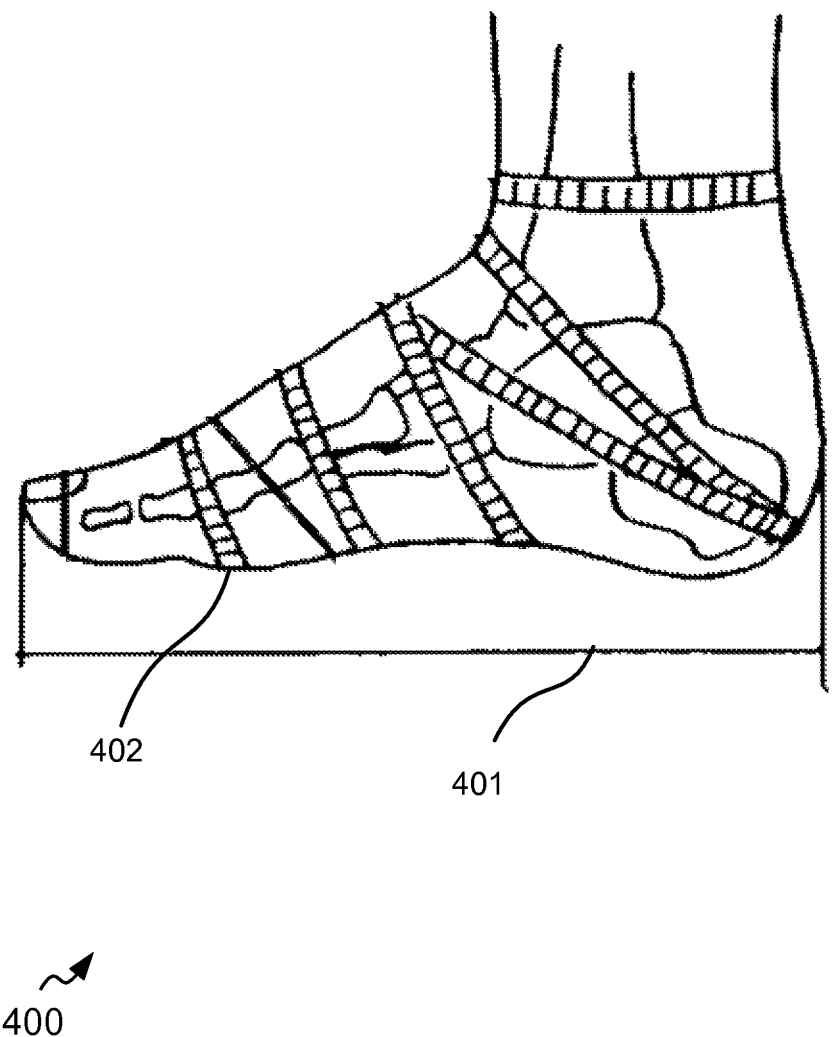
FIG. 4 illustrates an example diagram of foot measurements.

The apparatus 120 of foot measurement comprises a base plate 121 that is configured to receive a foot to be measured. As further illustrated in diagram 400 of FIG. 4, the foot has a first length 401 from a tip of a longest toe to a back of a heel, and a first circumference 402 around a ball of the foot. More specifically, the first circumference 402 is the circumference around the joints between toes and metatarsals. Accordingly, the first circumference 402 represents the largest circumference around the foot. The first circumference 402 is also known as girth.

The base plate 121 has a front end 121A and a back end 121B that are at a first distance 125 from each other. In other words, the first distance 125 represents the length dimension of the apparatus 120. The first distance 125 is larger than the first length 401 to allow comfortably positioning a foot to be measured on it. Similarly, a width of the apparatus 120 may be larger than the width of the foot to be measured. The back end 121B of the base plate 121 is configured to receive the back of the heel of the foot to be measured to enable determination of the first length 401 based on the first distance 125 and a second distance 126 between the front end 121A of the base plate 121 and the tip of the longest toe of the positioned foot. The foot to be measured may be positioned on the base plate 121 such that the longitudinal axis of the foot to be measured substantially aligns with the longitudinal axis of the base plate 121, and the back of the heel of the foot to be measured lays against the back end 121B of the base plate 121.

In an example, the apparatus 120 may comprise one or more side panels, e.g. substantially perpendicular to the base plate 121, as can be seen in FIG. 3B. The apparatus 120 may be manufactured e.g. out of cardboard, plastic, or the like. The apparatus 120 may be foldable e.g. to allow easy and efficient storage and delivery (such as in an envelope) to the user 110.

The apparatus 120 may further comprise a heel support or abutment 122 provided at the back end 121B of the base plate 121 to assist in positioning the foot to be measured on the base plate 121. The heel support 122 may be arranged substantially perpendicular to the base plate 121 e.g. such that when the base plate 121 is horizontal, the heel support 122 is substantially vertical.

The apparatus 120 comprises a single circumference measurement loop 123. That is, the circumference measurement loop 123 is the only circumference measurement loop in the apparatus 120. The circumference measurement loop 123 comprises a first portion 123A of elastic material and a second portion 123B of substantially non-elastic material. When the first portion 123A is non-stretched (i.e. when the circumference measurement loop 123 is empty with no foot inserted in it), the circumference measurement loop 123 has a second circumference that is smaller than the first circumference 402. The circumference measurement loop 123 is configured to encircle the foot to be measured at its ball in order to enable determination of the first circumference 402 based on the amount of stretch of the first portion 123A.

In an embodiment, the first portion 123A of the circumference measurement loop 123 may have a first visual characteristic and the second portion 123B of the circumference measurement loop 123 may have a second visual characteristic, such that the first visual characteristic is visually distinguishable from the second visual characteristic. For example, the first and second visual characteristics may comprise contrast, color, brightness and/or patterning. In an example, the second portion 123B may be substantially lighter than the first portion 123A, as shown in the embodiment of FIGS. 3A and 3B, or vice versa.

Optionally, the base plate 121 may comprise one or more coordination markers 124A-124F to assist in the determination of the first length 401 and/or in the determination of the first circumference 402.

FIG. 2 is a block diagram of the computing device 200 capable of implementing example embodiments described herein.

The computing device 200 comprises one or more processors 202, and one or more memories 204 that comprise computer program code 205. The computing device 200 may also include the digital camera 208, an input/output module 212, and/or a communication interface 214.

Although the communication device 200 is depicted to include only one processor 202, the communication device 200 may include more processors. In an embodiment, the memory 204 is capable of storing instructions 205, such an operating system and various applications, including the application 2051. Furthermore, the memory 204 may include a storage or database 206 that may be used e.g. to store one or more shoe sizing charts.

Furthermore, the processor 202 is capable of executing the stored instructions 205. In an embodiment, the processor 202 may be embodied as a multi-core processor, a single core processor, or a combination of one or more multi-core processors and one or more single core processors. For example, the processor 202 may be embodied as one or more of various processing devices, such as a coprocessor, a microprocessor, a controller, a digital signal processor (DSP), a processing circuitry with or without an accompanying DSP, or various other processing devices including integrated circuits such as, for example, an application specific integrated circuit (ASIC), a field programmable gate array (FPGA), a microcontroller unit (MCU), a hardware accelerator, a special-purpose computer chip, or the like. In an embodiment, the processor 202 may be configured to execute hard-coded functionality. In an embodiment, the processor 202 is embodied as an executor of software instructions, wherein the instructions may specifically configure the processor 202 to perform the algorithms and/or operations described herein when the instructions are executed.

The memory 204 may be embodied as one or more volatile memory devices, one or more non-volatile memory devices, and/or a combination of one or more volatile memory devices and non-volatile memory devices. For example, the memory 204 may be embodied as semiconductor memories (such as mask ROM, PROM (programmable ROM), EPROM (erasable PROM), flash ROM, RAM (random access memory), etc.).

The input/output module (hereinafter referred to as 'I/O module') 212 is configured to facilitate provisioning of an output and/or receiving an input. The I/O module 212 is configured to be in communication with the processor 202 and the memory 204. Examples of the I/O module 212 include, but are not limited to, an input interface and/or an output interface. Examples of the input interface may include, but are not limited to, a keypad, a touch screen, soft keys, and the like. Examples of the output interface may include, but are not limited to, a display such as a light emitting diode display, a thin-film transistor (TFT) display, a liquid crystal display, an active-matrix organic light-emitting diode (AMOLED) display, and the like. In an example embodiment, the processor 202 may include I/O circuitry configured to control at least some functions of one or more elements of the I/O module 212, such as, for example, a display, and/or the like, as well as the speaker 212 and/or the microphone 212. The processor 202 and/or the I/O circuitry may be configured to control one or more functions of the one or more elements of the I/O module 212 through computer program instructions, for example, software and/or firmware, stored on a memory, for example, the memory 204, and/or the like, accessible to the processor 202.

In an embodiment, the I/O module 212 may be configured to provide a user interface (UI) configured to provide options or any other display to a user of the computing device 200. In addition, the I/O module 212 may be integrated with mechanisms configured to receive inputs from the user of the computing device 200.

The communication interface 214 may enable the computing device 200 to communicate with other devices. In an embodiment, various components of the computing device 200, such as the processor 202, the memory 204, the I/O module 212 and the communication interface 214 are configured to communicate with each other via or through a centralized circuit 210. The centralized circuit 210 may be various devices configured to, among other things, provide or enable communication between the components 202-214 of the computing device 200. In certain embodiments, the centralized circuit 210 may be a central printed circuit board (PCB) such as a motherboard, a main board, an communication device board, or a logic board. The centralized circuit 210 may also, or alternatively, include other printed circuit assemblies (PCAs) or communication channel media.

The computing device 200 as illustrated and hereinafter described is merely illustrative of an apparatus that could benefit from embodiments of the invention and, therefore, should not be taken to limit the scope of the invention. It is noted that the computing device 200 may include fewer or more components than those depicted in FIG. 2.

As discussed above, the system 100 of foot measurement comprises the apparatus 120 of foot measurement. The system 100 further comprises the digital camera 208 that is configured to capture an image of the foot positioned on the apparatus 120. The image is captured such that it covers at least the stretched first portion 123A of the circumference measurement loop 123 and the second distance 126.

The system further comprises the computing device 200 that comprises the processor 202 and at least one memory 204 comprising computer program code 205. The at least one memory 204 and the computer program code 205 are configured to, with the at least one processor 202, cause the computing device 200 to obtain information about the first distance 125, the second circumference and a non-stretched length of the first portion 123A. For example, at least some of the first distance 125, the second circumference and the non-stretched length of the first portion 123A may be stored in the at least one memory 204 (e.g. in the database 206) from which they are obtained. For example, at least some of the first distance 125, the second circumference and the non-stretched length of the first portion 123A may be stored in a location external to the computing device 200 (such as the server device 140 and/or the database 145) from which they are obtained. When stored in the external location, at least some of the first distance 125, the second circumference and the non-stretched length of the first portion 123A may be obtained from the external location each time they are needed, or at least some of them may be obtained from the external location once and then stored locally in the computing device 200. In an embodiment, obtaining at least some of the first distance 125, the second circumference and the non-stretched length of the first portion 123A may comprise obtaining them via input from the user 110, after which at least some them may be stored locally or externally.

The at least one memory 204 and the computer program code 205 are further configured to, with the at least one processor 202, cause the computing device 200 to receive the image of the foot positioned on the apparatus 120 that was captured by the digital camera 208.

The at least one memory 204 and the computer program code 205 are further configured to, with the at least one processor 202, cause the computing device 200 to identify the second distance 126 and a stretched length of the first portion 123A from the received image. As discussed above, the second distance 126 is the distance between the front end 121A of the base plate 121 and the tip of the longest toe of the positioned foot. Since the captured and received image covers this area, it can be determined from the image e.g. with any suitable image analysis software or the like.

In an embodiment, to identify the stretched length of the first portion 123A from the captured and received image, the difference between the first visual characteristic of the first portion 123A of the circumference measurement loop 123 and the second visual characteristic of the second portion 123B of the circumference measurement loop 123 may be utilized to distinguish the first portion 123A from the second portion 123B. For example, the second portion 123B may be substantially lighter than the first portion 123A, as shown in the embodiment of FIGS. 3A and 3B, or vice versa, as discussed above. Since the stretched first portion 123A can be distinguished from the second portion 123B (as well as the positioned foot and the base plate 121) in the captured and received image, any suitable image analysis software or the like can be utilized to identify the stretched length of the first portion 123A.

The at least one memory 204 and the computer program code 205 are further configured to, with the at least one processor 202, cause the computing device 200 to determine the first length 401 (i.e. the length of the foot from the tip of the longest toe to the back of the heel) based on the difference between the obtained first distance 125 (i.e. the length of the apparatus 120) and the identified second distance 126.

The at least one memory 204 and the computer program code 205 are further configured to, with the at least one processor 202, cause the computing device 200 to determine the first circumference 402 (i.e. the circumference around the ball of the foot, that is, around the joints between toes and metatarsals) based on e.g. the sum of the obtained second circumference and a difference between the obtained non-stretched length of the first portion 123A and the identified stretched length of the first portion 123A.

Optionally, the at least one memory 204 and the computer program code 205 may be further configured to, with the at least one processor 202, cause the computing device 200 to access a predetermined shoe sizing chart (e.g. in the database 206 or database 145, as discussed above), compare the determined first length and first circumference to corresponding data in the accessed shoe sizing chart, and determine a shoe size for the foot based on the comparison. The shoe sizing chart may comprise e.g. a French shoe sizing chart, an English shoe sizing chart, or the like.

At least some of the embodiments of the system 100 store the input girths and lengths in millimeters. Furthermore, at least some of the embodiments of the system 100 can be used to measure, in shop or at home, the length and girth of the customer's foot thereby allowing combining the right products with the right feet. At least some of the embodiments allow measuring the foot from the same places (length and girth) where the industrial lasts are graded. When the millimeters from the girth and length of the foot are obtained, they can be compared to the millimeters of the girth and length of any industrial last regardless of what the sizing system is.

Figure 5:
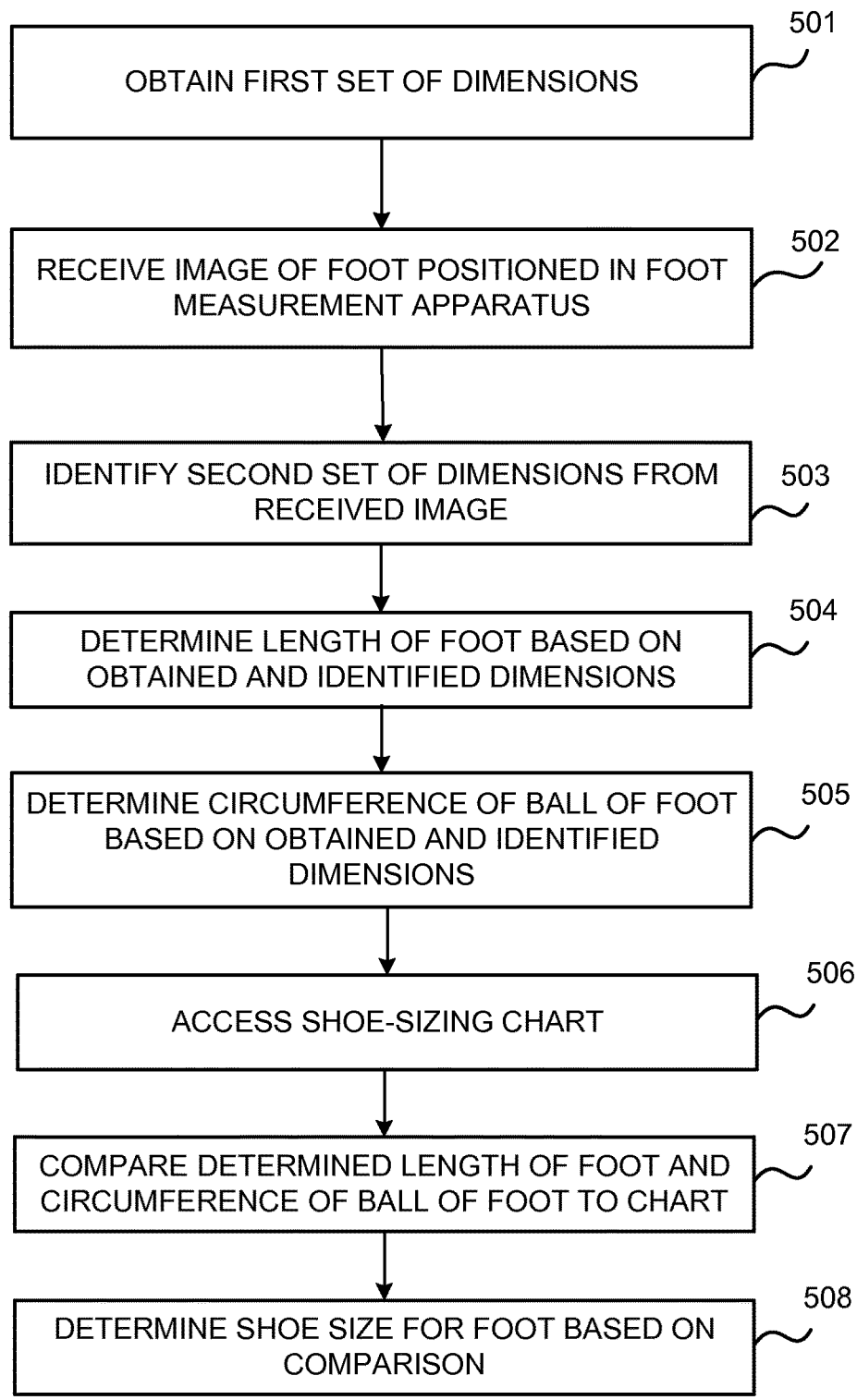
FIG. 5 illustrates an example flow diagram of a method of foot measurement, in accordance with an example embodiment.

FIG. 5 illustrates an example flow diagram of a method 500 of foot measurement, in accordance with an example embodiment.

At operation 501, information about a first distance 125, a second circumference and a non-stretched length of a first portion of the apparatus 120 of foot measurement is obtained by the computing device 200.

At operation 502, an image of a foot positioned on the apparatus 120 captured with the digital camera 208 is received at the computing device 200. The image covers at least the stretched first portion 123A of the circumference measurement loop 123 and the second distance 126. It is to be noted that operation 502 can alternatively be performed before operation 501.

At operation 503, the second distance 126 and a stretched length of the first portion 123A are identified by the computing device 200 from the received image.

At operation 504, the first length 401 is determined by the computing device 200 based on a difference between the obtained first distance 125 and the identified second distance 126.

At operation 505, the first circumference 402 is determined by the computing device 200 based on a sum of the obtained second circumference and a difference between the obtained non-stretched length of the first portion 123A and the identified stretched length of the first portion 123A.

At optional operation 506, a predetermined shoe sizing chart is accessed by the computing device 200.

At optional operation 507, the determined first length and first circumference are compared by the computing device 200 to corresponding data in the accessed shoe sizing chart.

At optional operation 508, a shoe size for the foot is determined by the computing device 200 based on the comparison.

The method 500 may be performed by the computing device 200 of FIG. 2. Further features of the method 500 directly result from the functionalities and parameters of the computing device 200 and the apparatus 120, and thus are not repeated here. The method 500 can be performed by computer program(s).

The exemplary embodiments can include, for example, any suitable computer devices and the like, capable of performing the processes of the exemplary embodiments. The devices and subsystems of the exemplary embodiments can communicate with each other using any suitable protocol and can be implemented using one or more programmed computer systems or devices.

One or more interface mechanisms can be used with the exemplary embodiments, including, for example, Internet access, telecommunications in any suitable form (e.g., voice, modem, and the like), wireless communications media, and the like. For example, employed communications networks or links can include one or more satellite communications networks, wireless communications networks, cellular communications networks, 3G communications networks, 4G communications networks, Public Switched Telephone Network (PSTNs), Packet Data Networks (PDNs), the Internet, intranets, a combination thereof, and the like.

It is to be understood that the exemplary embodiments are for exemplary purposes, as many variations of the specific hardware used to implement the exemplary embodiments are possible, as will be appreciated by those skilled in the hardware and/or software art(s). For example, the functionality of one or more of the components of the exemplary embodiments can be implemented via one or more hardware and/or software devices.

The exemplary embodiments can store information relating to various processes described herein. This information can be stored in one or more memories, such as a hard disk, optical disk, magneto-optical disk, RAM, and the like. One or more databases can store the information used to implement the exemplary embodiments of the present inventions. The databases can be organized using data structures (e.g., records, tables, arrays, fields, graphs, trees, lists, and the like) included in one or more memories or storage devices listed herein. The processes described with respect to the exemplary embodiments can include appropriate data structures for storing data collected and/or generated by the processes of the devices and subsystems of the exemplary embodiments in one or more databases.

All or a portion of the exemplary embodiments can be conveniently implemented using one or more general purpose processors, microprocessors, digital signal processors, micro-controllers, and the like, programmed according to the teachings of the exemplary embodiments of the present inventions, as will be appreciated by those skilled in the computer and/or software art(s). Appropriate software can be readily prepared by programmers of ordinary skill based on the teachings of the exemplary embodiments, as will be appreciated by those skilled in the software art. In addition, the exemplary embodiments can be implemented by the preparation of application-specific integrated circuits or by interconnecting an appropriate network of conventional component circuits, as will be appreciated by those skilled in the electrical art(s). Thus, the exemplary embodiments are not limited to any specific combination of hardware and/or software.

Stored on any one or on a combination of computer readable media, the exemplary embodiments of the present inventions can include software for controlling the components of the exemplary embodiments, for driving the components of the exemplary embodiments, for enabling the components of the exemplary embodiments to interact with a human user, and the like. Such software can include, but is not limited to, device drivers, firmware, operating systems, development tools, applications software, and the like. Such computer readable media further can include the computer program product of an embodiment of the present inventions for performing all or a portion (if processing is distributed) of the processing performed in implementing the inventions. Computer code devices of the exemplary embodiments of the present inventions can include any suitable interpretable or executable code mechanism, including but not limited to scripts, interpretable programs, dynamic link libraries (DLLs), Java classes and applets, complete executable programs, Common Passenger Request Broker Architecture (CORBA) passengers, and the like. Moreover, parts of the processing of the exemplary embodiments of the present inventions can be distributed for better performance, reliability, cost, and the like.

As stated above, the components of the exemplary embodiments can include computer readable medium or memories for holding instructions programmed according to the teachings of the present inventions and for holding data structures, tables, records, and/or other data described herein. Computer readable medium can include any suitable medium that participates in providing instructions to a processor for execution. Such a medium can take many forms, including but not limited to, non-volatile media, volatile media, and the like. Non-volatile media can include, for example, optical or magnetic disks, magneto-optical disks, and the like. Volatile media can include dynamic memories, and the like. Common forms of computer-readable media can include, for example, a floppy disk, a flexible disk, hard disk, or any other suitable medium from which a computer can read.

While the present inventions have been described in connection with a number of exemplary embodiments, and implementations, the present inventions are not so limited, but rather cover various modifications, and equivalent arrangements, which fall within the purview of prospective claims.

The invention claimed is:

1. An apparatus (120) of foot measurement, characterized in comprising:
a base plate (121) configured to receive a foot to be measured, the foot having a first length (401) from a tip of a longest toe to a back of a heel and a first circumference (402) around a ball of the foot, and the base plate (121) having a front end (121A) and a back end (121B) at a first distance (125) from each other, the first distance (125) being larger than the first length (401), the back end (121B) of the base plate (121) configured to receive the back of the heel of the foot to be measured to enable determination of the first length (401) based on the first distance (125) and a second distance (126) between the front end (121A) of the base plate (121) and the tip of the longest toe of the positioned foot; and a single circumference measurement loop (123), comprising a first portion (123A) of elastic material and a second portion (123B) of substantially non-elastic material, the circumference measurement loop (123) having, when non-stretched, a second circumference smaller than the first circumference (402), and the circumference measurement loop (123) configured to encircle the foot to be measured at its ball to enable determination of the first circumference (402) based on the amount of stretch of the first portion (123A), wherein the first portion (123A) of the circumference measurement loop (123) has a first visual characteristic and the second portion (123B) of the circumference measurement loop (123) has a second visual characteristic, the first visual characteristic being visually distinguishable from the second visual characteristic.

2. The apparatus (120) according to claim 1, wherein the first and second visual characteristics comprise at least one of contrast, color, brightness or patterning.

3. The apparatus (120) according to claim 1, wherein the base plate (121) comprises one or more coordination markers (124A-124F) to assist in at least one of the determination of the first length (401) or the determination of the first circumference (402).

4. The apparatus (120) according to claim 1, further comprising a heel support (122) provided at the back end (121B) of the base plate (121) to assist in positioning the foot to be measured on the base plate (121).

5. A system (100) of foot measurement, characterized in comprising:

the apparatus (120) according to claim 1;

a digital camera (208) configured to capture an image of a foot positioned on the apparatus (120), the image covering at least the stretched first portion (123A) of the circumference measurement loop (123) and the second distance (126); and a computing device (200) comprising at least one processor (202) and at least one memory (204) comprising computer program code (205), the at least one memory (204) and the computer program code (205) configured to, with the at least one processor (202), cause the computing device (200) to at least:

obtain information about the first distance (125), the second circumference and a non-stretched length of the first portion (123A);

receive the captured image;

identify the second distance (126) and a stretched length of the first portion (123A) from the received image, and in identifying the stretched length of the first portion (123A), utilize the difference between the first visual characteristic of the first portion (123A) of the circumference measurement loop (123) and the second visual characteristic of the second portion (123B) of the circumference measurement loop (123) to distinguish the first portion (123A) from the second portion (123B);

determine the first length (401) based on a difference between the obtained first distance (125) and the identified second distance (126); and determine the first circumference (402) based on a sum of the obtained second circumference and a difference between the obtained non-stretched length of the first portion (123A) and the identified stretched length of the first portion (123A).

6. The system (100) according to claim 5, wherein the at least one memory (204) and the computer program code (205) are further configured to, with the at least one processor (202), cause the computing device (200) to:

access a predetermined shoe sizing chart;

compare the determined first length (401) and first circumference (402) to corresponding data in the accessed shoe sizing chart; and determine a shoe size for the foot based on the comparison.

7. A method (500) of foot measurement, characterized in comprising:

obtaining (501), by a computing device (200), information about a first distance (125), a second circumference and a non-stretched length of a first portion (123A) of the apparatus (120) according to claim 1;

receiving (502), at the computing device (200), an image of a foot positioned on the apparatus (120) captured with a digital camera (208), the image covering at least the stretched first portion (123A) of the circumference measurement loop (123) and the second distance (126);

identifying (503), by the computing device (200), the second distance (126) and a stretched length of the first portion (123A) from the received image, wherein the identifying (503) of the stretched length of the first portion (123A) comprises utilizing the difference between the first visual characteristic of the first portion (123A) of the circumference measurement loop (123) and the second visual characteristic of the second portion (123B) of the circumference measurement loop (123) to distinguish the first portion (123A) from the second portion (123B);

determining (504), by the computing device (200), the first length (401) based on a difference between the obtained first distance (125) and the identified second distance (126); and determining (505), by the computing device (200), the first circumference (402) based on a sum of the obtained second circumference and a difference between the obtained non-stretched length of the first portion (123A) and the identified stretched length of the first portion (123A).

8. The method (500) according to claim 7, further comprising:

accessing (506), by the computing device (200), a predetermined shoe sizing chart;

comparing (507), by the computing device (200), the determined first length (401) and first circumference (402) to corresponding data in the accessed shoe sizing chart; and determining (508), by the computing device (200), a shoe size for the foot based on the comparison.

9. The apparatus (120) according to claim 2, wherein the base plate (121) comprises one or more coordination markers (124A-124F) to assist in at least one of the determination of the first length (401) or the determination of the first circumference (402).

10. The apparatus (120) according to claim 2, further comprising a heel support (122) provided at the back end (121B) of the base plate (121) to assist in positioning the foot to be measured on the base plate (121).

11. The apparatus (120) according to claim 3, further comprising a heel support (122) provided at the back end (121B) of the base plate (121) to assist in positioning the foot to be measured on the base plate (121).

12. A system (100) of foot measurement, characterized in comprising:

the apparatus (120) according to claim 2;
a digital camera (208) configured to capture an image of a foot positioned on the apparatus (120), the image covering at least the stretched first portion (123A) of the circumference measurement loop (123) and the second distance (126); and
a computing device (200) comprising at least one processor (202) and at least one memory (204) comprising computer program code (205), the at least one memory (204) and the computer program code (205) configured to, with the at least one processor (202), cause the computing device (200) to at least:
obtain information about the first distance (125), the second circumference and a non-stretched length of the first portion (123A);
receive the captured image;
identify the second distance (126) and a stretched length of the first portion (123A) from the received image, and in identifying the stretched length of the first portion (123A), utilize the difference between the first visual characteristic of the first portion (123A) of the circumference measurement loop (123) and the second visual characteristic of the second portion (123B) of the circumference measurement loop (123) to distinguish the first portion (123A) from the second portion (123B);
determine the first length (401) based on a difference between the obtained first distance (125) and the identified second distance (126); and
determine the first circumference (402) based on a sum of the obtained second circumference and a difference between the obtained non-stretched length of the first portion (123A) and the identified stretched length of the first portion (123A).

13. A system (100) of foot measurement, characterized in comprising:
the apparatus (120) according to claim 3;
a digital camera (208) configured to capture an image of a foot positioned on the apparatus (120), the image covering at least the stretched first portion (123A) of the circumference measurement loop (123) and the second distance (126); and
a computing device (200) comprising at least one processor (202) and at least one memory (204) comprising computer program code (205), the at least one memory (204) and the computer program code (205) configured to, with the at least one processor (202), cause the computing device (200) to at least:
obtain information about the first distance (125), the second circumference and a non-stretched length of the first portion (123A);
receive the captured image;
identify the second distance (126) and a stretched length of the first portion (123A) from the received image, and in identifying the stretched length of the first portion (123A), utilize the difference between the first visual characteristic of the first portion (123A) of the circumference measurement loop (123) and the second visual characteristic of the second portion (123B) of the circumference measurement loop (123) to distinguish the first portion (123A) from the second portion (123B);
determine the first length (401) based on a difference between the obtained first distance (125) and the identified second distance (126); and
determine the first circumference (402) based on a sum of the obtained second circumference and a difference between the obtained non-stretched length of the first portion (123A) and the identified stretched length of the first portion (123A).

14. A system (100) of foot measurement, characterized in comprising:
the apparatus (120) according to claim 4;
a digital camera (208) configured to capture an image of a foot positioned on the apparatus (120), the image covering at least the stretched first portion (123A) of the circumference measurement loop (123) and the second distance (126); and
a computing device (200) comprising at least one processor (202) and at least one memory (204) comprising computer program code (205), the at least one memory (204) and the computer program code (205) configured to, with the at least one processor (202), cause the computing device (200) to at least:
obtain information about the first distance (125), the second circumference and a non-stretched length of the first portion (123A);
receive the captured image;
identify the second distance (126) and a stretched length of the first portion (123A) from the received image, and in identifying the stretched length of the first portion (123A), utilize the difference between the first visual characteristic of the first portion (123A) of the circumference measurement loop (123) and the second visual characteristic of the second portion (123B) of the circumference measurement loop (123) to distinguish the first portion (123A) from the second portion (123B);
determine the first length (401) based on a difference between the obtained first distance (125) and the identified second distance (126); and
determine the first circumference (402) based on a sum of the obtained second circumference and a difference between the obtained non-stretched length of the first portion (123A) and the identified stretched length of the first portion (123A).

15. A method (500) of foot measurement, characterized in comprising:
obtaining (501), by a computing device (200), information about a first distance (125), a second circumference and a non-stretched length of a first portion (123A) of the apparatus (120) according to claim 2;
receiving (502), at the computing device (200), an image of a foot positioned on the apparatus (120) captured with a digital camera (208), the image covering at least the stretched first portion (123A) of the circumference measurement loop (123) and the second distance (126);
identifying (503), by the computing device (200), the second distance (126) and a stretched length of the first portion (123A) from the received image, wherein the identifying (503) of the stretched length of the first portion (123A) comprises utilizing the difference between the first visual characteristic of the first portion (123A) of the circumference measurement loop (123) and the second visual characteristic of the second portion (123B) of the circumference measurement loop (123) to distinguish the first portion (123A) from the second portion (123B);
determining (504), by the computing device (200), the first length (401) based on a difference between the obtained first distance (125) and the identified second distance (126); and
determining (505), by the computing device (200), the first circumference (402) based on a sum of the obtained second circumference and a difference between the obtained non-stretched length of the first portion (123A) and the identified stretched length of the first portion (123A).

16. A method (500) of foot measurement, characterized in comprising:
    obtaining (501), by a computing device (200), information about a first distance (125), a second circumference and a non-stretched length of a first portion (123A) of the apparatus (120) according to claim 3;
    receiving (502), at the computing device (200), an image of a foot positioned on the apparatus (120) captured with a digital camera (208), the image covering at least the stretched first portion (123A) of the circumference measurement loop (123) and the second distance (126);
    identifying (503), by the computing device (200), the second distance (126) and a stretched length of the first portion (123A) from the received image, wherein the identifying (503) of the stretched length of the first portion (123A) comprises utilizing the difference between the first visual characteristic of the first portion (123A) of the circumference measurement loop (123) and the second visual characteristic of the second portion (123B) of the circumference measurement loop (123) to distinguish the first portion (123A) from the second portion (123B);
    determining (504), by the computing device (200), the first length (401) based on a difference between the obtained first distance (125) and the identified second distance (126); and
    determining (505), by the computing device (200), the first circumference (402) based on a sum of the obtained second circumference and a difference between the obtained non-stretched length of the first portion (123A) and the identified stretched length of the first portion (123A).

17. A method (500) of foot measurement, characterized in comprising:
    obtaining (501), by a computing device (200), information about a first distance (125), a second circumference and a non-stretched length of a first portion (123A) of the apparatus (120) according to claim 4;
    receiving (502), at the computing device (200), an image of a foot positioned on the apparatus (120) captured with a digital camera (208), the image covering at least the stretched first portion (123A) of the circumference measurement loop (123) and the second distance (126);
    identifying (503), by the computing device (200), the second distance (126) and a stretched length of the first portion (123A) from the received image, wherein the identifying (503) of the stretched length of the first portion (123A) comprises utilizing the difference between the first visual characteristic of the first portion (123A) of the circumference measurement loop (123) and the second visual characteristic of the second portion (123B) of the circumference measurement loop (123) to distinguish the first portion (123A) from the second portion (123B);
    determining (504), by the computing device (200), the first length (401) based on a difference between the obtained first distance (125) and the identified second distance (126); and
    determining (505), by the computing device (200), the first circumference (402) based on a sum of the obtained second circumference and a difference between the obtained non-stretched length of the first portion (123A) and the identified stretched length of the first portion (123A).

\* \* \* \* \*